US00PP20556P2

(12) United States Plant Patent
Giesen

(10) Patent No.: US PP20,556 P2
(45) Date of Patent: Dec. 15, 2009

(54) ***NEMESIA* PLANT NAMED 'CNEM WHIT'**

(50) Latin Name: ***Nemesia fruticosa*, syn. *N. fruticans***
Varietal Denomination: Cnem Whit

(75) Inventor: Eric Giesen, Andijk (NL)

(73) Assignee: Goldsmith Seeds Europe B.V. (NL)

( * ) Notice: Subject to any disclaimer, the term of this patent is extended or adjusted under 35 U.S.C. 154(b) by 0 days.

(21) Appl. No.: 12/290,976

(22) Filed: Nov. 5, 2008

(51) Int. Cl.
*A01H 5/00* (2006.01)

(52) U.S. Cl. ..... Plt./458

(58) Field of Classification Search ..... Plt./458
See application file for complete search history.

*Primary Examiner*—Annette H Para
(74) *Attorney, Agent, or Firm*—S. Matthew Edwards

(57) ABSTRACT

A new *Nemesia* plant named 'Cnem Whit,' particularly distinguished by the white flowers, a relatively compact growth habit that is semi-spreading and mounding, strong stems, full well branched plant with medium-green foliage, good floriferiousness, and a slightly sweet fragrance.

1 Drawing Sheet

Latin name of the genus and species of the plant claimed: *Nemesia fruticosa*, syn. *N. fruticans.*

Varietal denomination: 'Cnem Whit'.

BACKGROUND OF THE NEW PLANT

The present invention comprises a new *Nemesia*, botanically known as *Nemesia fruticosa* and hereinafter referred to by the variety name 'Cnem Whit.'

'Cnem Whit' is a product of a planned breeding program. The new cultivar 'Cnem Whit' has white flowers, a relatively compact growth habit that is semi-spreading and mounded, strong stems, full well branched plant with medium-green foliage, good floriferiousness, and a slightly sweet fragrance.

'Cnem Whit' originated from a hybridization in a controlled breeding program in Andijk, Netherlands. The female parent was an unpatented hybrid seedling identified as 'NE05–117–1' with white color. 'NE05–117–1' has lighter green leaves and larger and fewer flowers than 'Cnem Whit.'

The male parent of 'Cnem Whit' was an unpatented hybrid seedling identified as 'NE05-117-1' with white color. 'NE05-117-1' has a more upright plant habit, longer peduncles, and smaller flowers than 'Cnem Whit.'

'Cnem Whit' was selected as one flowering plant within the progeny of the stated cross in January 2006 in a controlled environment in Andijk, Netherlands. The pollination took place in June 2005 and the seed sowing in October 2005.

The first act of asexual reproduction of 'Cnem Whit' was accomplished when vegetative cuttings taken from the initial selection in the January 2006 in a controlled environment in Andijk, Netherlands.

Horticultural examination of plants grown from cuttings of the plant initiated in January 2006 in Andijk, Netherlands, and continuing thereafter, has demonstrated that the combination of characteristics as herein disclosed for 'Cnem Whit' are firmly fixed and are retained through successive generations of asexual reproduction.

'Cnem Whit' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cnem Whit' has not been made publicly available more than one year prior to the filing of this application.

DESCRIPTION OF THE DRAWINGS

The accompanying photographic drawing shows typical flower and foliage characteristics of 'Cnem Whit' with colors being as true as possible with an illustration of this type. The photographic drawing shows 2 flowering potted plants of the new variety in a gallon pot, and a close-up of the flowers. Both of the photographs were taken in April 2008 in Gilroy, Calif. USA. Both were grown in Gilroy, Calif. USA and were approximately 4–5 months old.

DETAILED BOTANICAL DESCRIPTION

The measurements were taken on May 27, 2008 (week 22) on plants that were growing in 12 cm plastic pots. Culture of these plants started around Feb. 1, 2008 (weeks 5–6) in Hillscheid, Germany. The plants were nearly 4 months old.

Color Chart used: Royal Horticultural Society Colour Chart (R.H.S.) 2001

BRIEF SUMMARY OF INVENTION

The following observations, measurements, and comparisons describe plants grown outside in Hillscheid, Germany. The following traits have been repeatedly observed and are determined to be basic characteristics of the new variety. The combination of these characteristics distinguishes this *Nemesia* as a new and distinct variety.

TABLE 1

DIFFERENCES BETWEEN THE NEW VARIETY 'CNEM WHIT' AND A SIMILAR VARIETY

| | 'Cnem Whit' | 'Nemhswhi' (U.S. Plant Pat. No. 16,569) |
|---|---|---|
| Flower size | Larger | Smaller |
| Plant habit | More upright | Less upright, more spreading |
| Foliage color | Darker green | Lighter green |

Plant:

*Form, growth and habit.*—Relatively compact, semi-spreading, mounded, and well branched plant.

*Plant height.*—13–16 cm.

*Plant height* (*inflorescence included*).—28–30 cm.

*Plant width.*—42–45 cm.

Foliage:

*Arrangement.*—Single, opposite and sessile.

*Immature, leaf color, upper surface.*—Between RHS 137D and RHS 143A.

*Lower surface.*—RHS 138B.

*Mature, leaf color, upper surface.*—From RHS 138A to RHS 138B.

*Lower surface.*—RHS 138B.

*Length.*—3.5–4.5 cm.

*Width.*—1.5–2.2 cm.

*Shape.*—Subulate to narrowly deltoid.

*Base shape.*—Truncate to weakly rounded.

*Apex shape.*—Acute.

*Margin.*—Weakly serrate.

*Texture.*—Glabrous.

*Color of veins, upper surface.*—Indistinct.

*Color of veins, lower surface.*—RHS 144B.

Stem:

*Color of stem.*—RHS 143C.

*Length of stem.*—19–24 cm.

*Diameter.*—0.2–0.3 cm.

*Length of internodes.*—2.5–3.5 cm.

*Texture.*—Glabrous with very short and fine pubescence.

Inflorescence:

*Type.*—Terminal raceme with flowers in an alternate and sometimes opposite arrangement. Most often three inflorescences at the end of a flowering stem, the middle one being primary and longest inflorescence.

*Blooming habit.*—Continuous flowering throughout the summer and into fall in some areas.

*Number of open flowers per inflorescence.*—About 9–11.

*Quantity of inflorescences per plant.*—80–100.

*Lastingness of individual blooms on the plant.*—About 6–7 days depending on temperatures.

*Fragrance.*—Slightly sweet.

*Color of peduncle.*—RHS 137D.

*Length of peduncle.*—12–17 cm.

*Texture.*—Sparse short hairs.

*Color of pedicel.*—RHS 144B.

*Length of pedicel.*—0.7–1.0 cm.

*Diameter of pedicel.*—0.1 cm.

*Texture.*—Finely pubescence, and few glandular hairs.

Corolla:

*Form.*—Single, zygomorphic, 5-lobed, fused at the base, somewhat reflexed; 2 lower lobes fused to each other to form a lip; spurred.

*Length of flower.*—1.8–2.1 cm.

*Width of flower.*—1.4–1.6 cm.

*Depth of flower.*—0.5–0.6 cm.

*Color petals, upper surface.*—Whiter than RHS 155A.

Color lower petals, upper surface.—Whiter than RHS 155A; lower petals have a basal yellow blotch of RHS 3A to B.

*Color all petals, lower surface.*—Whiter than RHS 155A.

*Length of upper petals.*—1.2–1.3 cm.

*Width of upper petals.*—1.7 cm.

*Length of lower petals.*—0.9–1.0 cm.

*Width of lower petals.*—0.8–0.9 cm.

*Petal shape.*—Oval.

*Apex shape.*—Rounded, and the upper middle lobe is slightly divided.

*Margin.*—Papillose.

*Color of spur.*—RHS 11B to RHS 11C, with RHS 11D at the tip.

*Length of spur.*—0.7–0.8 cm.

*Width of spur.*—0.1–0.2 cm.

Bud (just before opening):

*Color.*—Ranging from RHS 155A to RHS 155D.

*Length of bud.*—0.5–0.6 cm.

*Width of bud.*—0.4 cm.

*Shape.*—Round to ovate.

*Number of sepals.*—5.

*Color of sepals.*—RHS 143C with no anthocyanins.

*Length of sepals.*—0.25 cm.

*Width of sepals.*—0.15 cm.

*Sepal shape.*—Deltoid to lanceolate.

*Apex shape.*—Acute.

*Margins.*—Entire.

*Texture.*—Densely pubescent; few glandular hairs.

Reproductive organs:

*Pistil.*—One.

*Length.*—0.3–0.4 cm.

*Style color.*—RHS 157D.

*Style length.*—0.1–0.2 cm.

*Stigma color.*—RHS 157A.

*Number of stamen.*—4; 2 pairs with anthers coherent that are bowed or arching over and around the pistil.

*Color of filaments.*—RHS 155A or slightly RHS 157A.

*Length of filaments.*—One pair 0.4–0.5 cm and another pair 0.3 cm.

*Anther color.*—RHS 13D.

*Pollen amount.*—Moderate.

*Color of pollen.*—RHS 8A.

*Fertility/seed set.*—Not observed on this hybrid.

Disease/pest resistance: Disease resistance or susceptibility has not been observed on this hybrid.

What is claimed is:

1. A new and distinct variety of *Nemesia* plant named 'Cnem Whit,' substantially as illustrated and described herein.

* * * * *

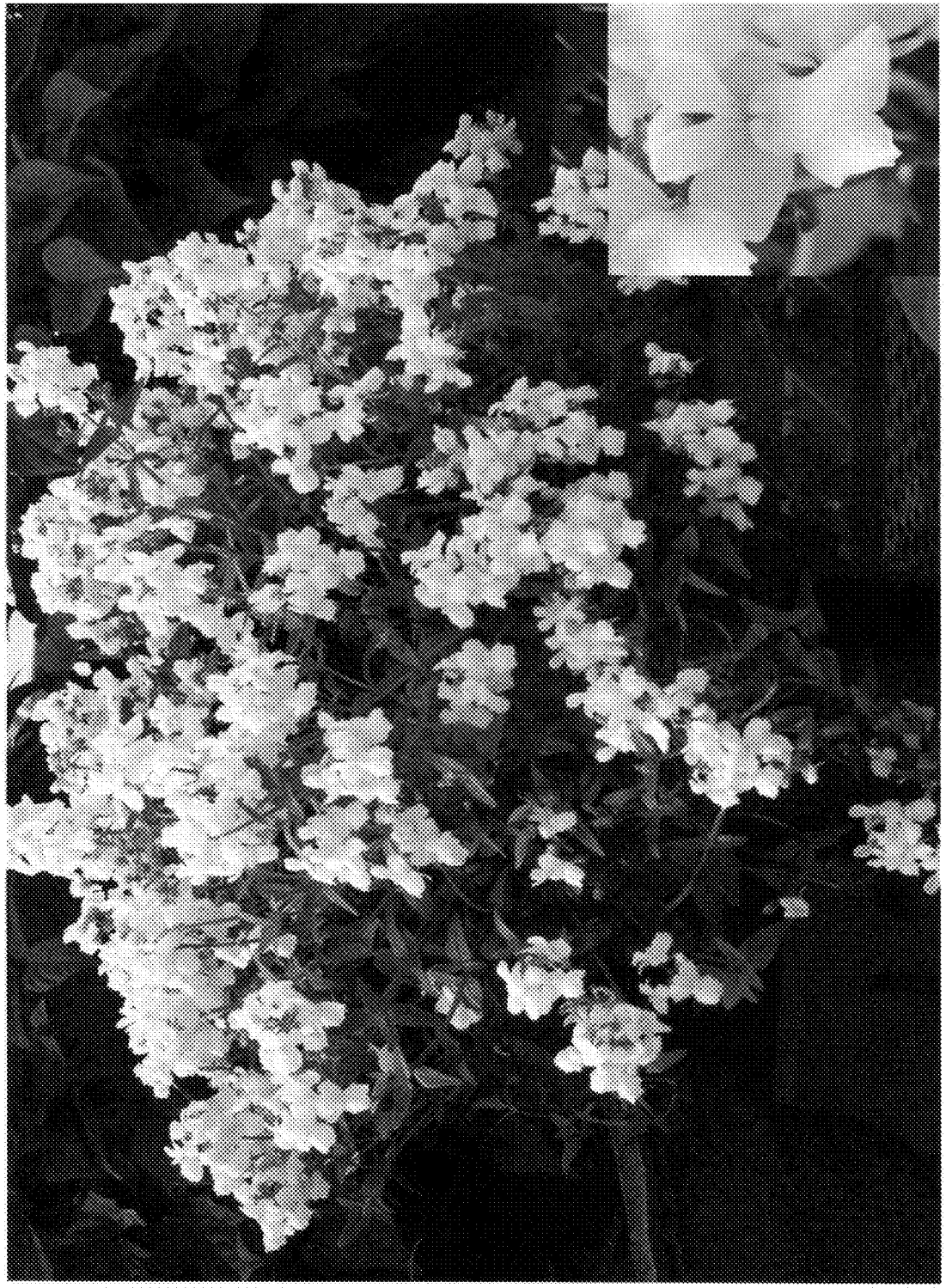

UNITED STATES PATENT AND TRADEMARK OFFICE

CERTIFICATE OF CORRECTION

PATENT NO. : PP 20,556 P2
APPLICATION NO. : 12/290976
DATED : December 15, 2009
INVENTOR(S) : Giesen It is certified that error appears in the above-identified patent and that said Letters Patent is hereby corrected as shown below:

At column 1, line 22, delete "NE05-117-1" and insert therefor --'NE04-100-1'--

At column 1, lines 22 and 23, delete "NE05-117-1" and insert therefor --'NE04-100-1'--

Signed and Sealed this

Second Day of February, 2010

David J. Kappos

David J. Kappos
*Director of the United States Patent and Trademark Office*